United States Patent [19]

Laukien et al.

[11] Patent Number: 5,505,832
[45] Date of Patent: Apr. 9, 1996

[54] DEVICE AND METHOD FOR MASS SPECTROMETRIC ANALYSIS OF SUBSTANCE MIXTURES BY COUPLING CAPILLARY ELECTROPHORETIC SEPARATION (CE) WITH ELECTROSPRAY IONIZATION (ESI)

[75] Inventors: Frank Laukien, Lincoln, Mass.; Jochen Franzen, Bremen, Germany

[73] Assignee: Bruker Franzen Analytik GmbH, Bremen, Germany

[21] Appl. No.: 432,860

[22] Filed: May 2, 1995

[30] Foreign Application Priority Data

May 2, 1994 [DE] Germany ............... 44 15 480.1

[51] Int. Cl.$^6$ ............ G01N 27/26; G01N 27/447; H01J 49/04; H01J 49/10
[52] U.S. Cl. ............... 204/452; 204/603; 250/288
[58] Field of Search ............... 204/299 R, 180.1; 250/288

[56] References Cited

U.S. PATENT DOCUMENTS

| | | | |
|---|---|---|---|
| 4,842,701 | 6/1989 | Smith et al. | 204/180.1 |
| 4,885,076 | 12/1989 | Smith et al. | 204/299 R |
| 4,963,736 | 10/1990 | Douglas et al. | 250/288 X |
| 4,994,165 | 2/1991 | Lee et al. | 204/299 R |
| 4,999,493 | 3/1991 | Allen et al. | 250/288 |
| 5,015,845 | 5/1991 | Allen et al. | 250/288 |
| 5,073,713 | 12/1991 | Smith et al. | 250/282 |
| 5,115,131 | 5/1992 | Jorgenson et al. | 250/288 |
| 5,170,052 | 12/1992 | Kato | 250/288 |
| 5,170,053 | 12/1992 | Hail et al. | 250/288 |
| 5,268,572 | 12/1993 | Mordehai et al. | 250/289 |
| 5,298,743 | 3/1994 | Kato | 250/288 |
| 5,306,412 | 4/1994 | Whitehouse et al. | 204/299 R |
| 5,310,463 | 5/1994 | Dadoo et al. | 204/180.1 |
| 5,349,186 | 9/1994 | Ikonomou et al. | 250/288 |
| 5,352,891 | 10/1994 | Monnig et al. | 250/282 |
| 5,352,892 | 10/1994 | Mordehai et al. | 250/288 |
| 5,393,975 | 2/1995 | Hail et al. | 250/288 |
| 5,423,964 | 6/1995 | Smith et al. | 204/180.1 |
| 5,436,446 | 7/1995 | Jarrell et al. | 250/288 |

*Primary Examiner*—John Niebling
*Assistant Examiner*—John S. Starsiak, Jr.

[57] ABSTRACT

The invention relates to a device and a method for mass-spectrometric analysis of substance samples which have been separated by capillary electrophoresis, particularly proteins, proteoglycanes or other protein conjugates, with ionization of the substance samples by a particularly substance-saving form of electrospraying. A method of "microspraying" is used which permits a flow of spray liquid of only several tens of nanoliters per minute in stable spray operation. The invention consists in a loose coupling of the spray capillary to the electrophoresis capillary in a liquid environment.

14 Claims, 1 Drawing Sheet

DEVICE AND METHOD FOR MASS SPECTROMETRIC ANALYSIS OF SUBSTANCE MIXTURES BY COUPLING CAPILLARY ELECTROPHORETIC SEPARATION (CE) WITH ELECTROSPRAY IONIZATION (ESI)

BACKGROUND OF THE INVENTION

1. Field of the Invention

The invention relates to a device and a method for mass spectrometric analysis of substance samples separated by capillary electrophoresis, particularly proteins, proteoglycanes or other protein conjugates, in which the substance samples are ionised by electrospraying. Such a method is known, among others, from the paper by M. A. Moseley et al. in J. Am. Soc. Mass Spectrom. 3,289 (1992).

2. Description of the Related Art

Various types of capillary electrophoresis are known, for example, capillary zone electrophoresis (CZE), capillary gel electrophoresis (CGE), capillary isotachophoreses (ITP) and others. The detailed differences in the various methods are not relevant to this invention. The various methods of charging the capillaries, with and without substance focusing are not relevant here either. A good overview of these methods can be obtained from the overview articles by Ring-Ling Chien and Dean S. Burgi, Anal. Chem. 64, 489A (1992) and by M. Albin, P. D. Grossman and S. E. Moring, Anal. Chem. 65, 489A (1993). The latest literature is given in the overview by C. Schöneich et al., Anal. Chem. 65, 67R (1993).

The common feature of these methods is that a solution comprising a mixture of substances (normally heavy molecules, and in particular, biomolecules) is introduced into a capillary, subjected to the effect of a relatively strong electric field in the electrolytic liquid with which the capillary is filled, and begin to migrate. The rate of migration of the mixture components depends on the substance. As in chromatography a separation of substances takes place. The reason for this migration is that the charge of the biomolecules depending on pH.

By contrast with other methods of separation such as liquid chromatography, capillary electrophoresis, particularly capillary zone electrophoresis, has the great advantage of achieving extremely good separations in a short separation time. In this way separations with more than one million theoretical plates can be obtained in less than 20 minutes and plate numbers over 100,000 in less than a minute.

Normally each end of the capillary is in a liquid reservoir in which there are also electrodes supplying the electrophoresis voltage. Just before the second liquid reservoir there is usually a detection device which measures the separated substances during the flow through the capillary by absorption of visible or ultraviolet light in the capillary.

In the electrophoretic capillary there are three partial electric currents flowing: (1) the electrolytic current through the migrating analyte ions, the charge of which depends on the pH of the solution, (2) an electroosmotic current due to the effect of stationary wall charges on the solution, and (3) an electrolytic current usually with a high value, due to pH-determining acids, bases or salts of the solution. All types of capillary electrophoresis have the advantage that the ohmic heat which results from these currents is very efficiently dissipated by the capillary walls so relatively large current densities become possible.

The electroosmotic effect consists of mobile charges being induced in the liquid by stationary wall charges which arise due to the electrolyte, these charges generating an electric current due to the difference in potential but also generating an electroosmotic liquid current. Due to the electroosmotic liquid current the liquid is pumped through the capillary in small quantities. The direction and magnitude of the liquid current depends on the type of wall charges, capillary diameter, field strength, and the polarity of the electric field.

The wall charges can be influenced by coating the capillary wall with polymers. For example, in an uncoated quartz capillary negative wall charges are generated. If certain organic compounds are bound to the wall, for example by aminopropylsilylation, positive wall charges can be generated. To prevent the analyte substances from being adsorbed by the wall and to ensure good electrophoretic separation it is important to create the same charge polarity of wall charges and analyte ions. For good separation of proteins in an acidified electrolyte which creates a positive charge in the protein molecules due to attachment of H+ ions, positive wall charges must also be generated because only then are the substance ions kept away from the walls by the Coulomb forces.

The electroosmotic flow is generally quite small but it can build up substantial pressure, although the pressure can be compensated by hydrostatic back pressure if one wishes to generate a certain flow of liquid by force. However, the electroosmotic current is generally well below 0.3 microliters per minute in a capillary with an inside diameter of 75 micrometers and the velocity of flow only seldom reaches the migration rate of the slowest substance molecules.

A good overview of electrospray ionization and the current state of the art is provided in the following review article: J. B. Fenn, M. Mann, C. K. Meng, S. F. Wong and C. M. Whitehouse; Spectr. Rev. 9, 37 (1990).

In the electrospray method a voltage of several kilovolts is applied between a conductive capillary and a flat surface, which are approximately 20 to 50 millimetres apart. Liquid in the capillary is dielectrically polarized under the effect of the electric field at the end of the capillary and is pulled out into a cone, the so-called Taylor cone. At the tip of this cone the surface tension of the liquid can no longer withstand the attraction of the electric field so a small droplet, which is electrically charged because of the dielectric polarization, falls off. The charged droplet flies toward the flat counter-electrode under the effect of the inhomogeneous electric field, initially with a high level of acceleration, but it is decelerated in the ambient air. During flight there is considerable evaporation on the surface of the droplet. If the liquid contains some relatively large molecules which can be more easily charged (ionized) than the molecules of the liquid due to electron removal, electron attraction, protonation or other means, in a favourable case the larger molecules may remain in an ionized form after complete evaporation of the liquid. The ionized molecules continue to fly towards the counter-electrode under the effect of the electric field due to the familiar process of "ion mobility" and can be transferred to the vacuum system of a mass spectrometer through a fine aperture or through a capillary.

Detachment of the droplets takes place at an exceptionally fast rate, depending on the supply of liquid in the capillary, so a continuous ion current is usually created. The supply is maintained by a very consistent pump, usually a syringe pump. In this process the larger molecules are usually not only charged once but many times. As a rough guideline, the average number of charges is higher, the larger the molecule. Large biomolecule ions can be charged 10 to 50 times. The charge is usually a protonation, i.e. binding with charged hydrogen atoms H+. For this reason ionization is also considerably dependent on the hydrogen ion concentration (i.e. on pH) of the solution. There is usually a wide distribution of ions with different numbers of charges.

Multiple charging of a relatively large molecule ion and the wide charge distribution are particularly favourable for detection purposes on the one hand. Since most mass spectrometers have a limited range of masses (or more precisely: a limited range of mass-to-charge ratios), one can still detect very large molecules far beyond the mass range defined for singly charged ions despite this limitation because the electrospray ions are charged many times. Due to the weight and regular distribution of the number of charges over the molecule ions of the same mass it is also easily possible to determine the molecular mass by calculation (M. Mann, C. K. Meng and J. B. Fenn, Anal. Chem. 61, 1702 (1989)).

With this conventional method using metal capillaries the droplets have a self-adjusting diameter of one to two micrometers, which depends on the dielectric constant, viscosity, flow rate, and surface tension of the liquid. Stable operation of electrospraying can only be maintained if the liquid flow is greater than about one microliter per minute. In addition, stable operation depends on the properties of the spray liquid, including pH, viscosity, surface tension, and conductivity. It is only in narrow tolerance ranges of these parameters that stable spraying is possible.

U.S. patent application Ser. No. 08/402,125, filed Mar. 10, 1995, the contents of which are incorporated herein by reference, discloses a method of electrospray ionization which leads to much smaller droplet sizes, more stable operation, and lower liquid flow. In this method, which hereinafter will be referred to as "microspraying" glass capillaries are used which have been pulled out to form very fine tips with aperture diameters of only approximately 2.5 micrometers. In completely stable operation the glass capillaries supply droplets with a diameter of approximately 100 to 200 nanometers, which, due to their high vapour pressure, reduced cooling due to evaporation, and their low mass, completely evaporate over a flight distance of only 1.5 millimetres even at room temperature.

It is a particular feature of this microspraying method that the method may be carried out without any liquid pump, as is used in all conventional methods. The supply of solution is achieved solely by the electrical forces of attraction with low-viscosity liquids. With higher-viscosity liquids a slight gas overpressure at the end of the capillary was sufficient for a self-regulating afterflow. The gas pressure does not need to be, and should not be, so high that when the spraying process is switched off liquid escapes from the capillary. The self-regulating supply of liquid is essential for stable operation of spraying at such low flow rates.

Further advantages of this method are that the spray voltage is only approximately 600 to 800 volts and that the spraying can easily be completely discontinued by reducing this voltage by a few hundred volts. Particularly with storage mass spectrometers such as high frequency quadrupole ion trap and ion cyclotron resonance spectrometers it is thus possible to develop analyte-conserving methods in which the spray ion beam is only switched on during the filling cycle of the ion traps and remains switched off in the analysis cycle.

However, the most important advantage of microspraying is the tolerance of the method of substantial changes in the electrolytic or viscous properties of the liquid. It is possible to spray extremely clean water, acids and bases in a pH range of 0.2 to 10. Even adding large quantities of organic solvents such as methanol or acetonitrile does not prevent stable spraying whilst the classic method of electrospraying is only in very narrow tolerance ranges for all these parameters.

Over the short distance to the counter-electrode the spray jet manifests only a very low divergence of approximately 200 micrometers so practically all the ions can be transferred to the vacuum of the mass spectrometer through a fine capillary.

Compared with a conventional electrospray unit which uses a solution having the same concentration, the ion current in the mass spectrometer is about two to three times higher. However, solvent flow, and hence analyte consumption, is 40 times lower than the lowest stable flow which can be set in conventional methods. The flow rate is only 25 nanoliters per minute. The yield of ions, measured by the quantity of analyte used, is therefore 100 higher.

Any type of mass spectrometer can in principle be used for analyzing the spray ions because the continuous generation of ions imposes no restrictions whatsoever. Both the classic sector field spectrometers and quadrupole spectrometers can be used, both types even in a tandem arrangement so as to be able to perform MS/MS analyses. Time-of-flight mass spectrometers need an outpulsing of the ion current shot in transversely but they can then be used to advantage. The yield of ions reaching the measuring process is higher than with the sector field or quadrupole spectrometers each acting as a filter for a single mass measured.

In this context, storage mass spectrometers such as quadrupole ion traps or ion cyclotron resonance units are particularly favourable. Since the microspray method can be switched off the ion current only needs to be switched on when the storage cell has to be filled with ions.

The aims of mass spectrometric analyses can vary enormously. The simplest are accurate determinations of the molecular weights of materials proteins in mixtures, or identification of proteins or proteoglycanes by determining the molecular weight of the enzymatically generated decomposition products such as peptides or oligosaccharides. The more difficult analyses include determinations of the amino acid sequences via MS/MS methods or analyses of the tertiary structures of large biomolecules.

Classic electrospray ionization and the new microspray method have a major disadvantage for analyzing substance mixtures: due to the wide distribution of charge states the scans have many lines. If the substance is pure, this is advantageous, as described above, because it is easy to determine the molecular weight using the regular rhythm of lines. Even with three simultaneously ionized substances the pattern can still be decoded from the superimposed scans. When more than three substances are superimposed the scan soon becomes very confusing though. Consequently, mixture analysis, as particularly occurs frequently with biomolecules, must always be preceded by a more or less complete separation of the substances. For this reason it would seem advisable to couple with a separating method.

Coupling capillary zone electrophoresis with electrospray ionization and mass spectrometric detection was described in the paper by M. A. Moseley et al. in J. Am. Soc. Mass Spectrom. 3, 289 (1992) mentioned above. That paper also refers to previous literature. It was a particular aim of this paper to examine the influence of various liquid parameters on electrospraying.

In the Moseley paper quoted, capillary electrophoresis was coupled only with the classic electrospray method but not with microspraying. It was always capillary zone electrophoresis which was used. To compensate for the electroosmotic liquid flows in various directions, a liquid current was usually set by fixing a pressure difference at both ends of the capillary. However, this flow is generally much too small for stable electrospraying so an excess of additional liquid current was fed coaxially to the electrospraying in all previous work. The electrophoresis capillary was inserted directed into the metal capillary for the additional liquid. In the quoted paper by Moseley et al. the electrophoresis capillary was allowed to project at the point of spraying by approximately 0.2 millimetres. The excess current of added liquid was used to set the spray parameters correctly.

As the analyses by Moseley et al. have indicated, the setting of optimal spray parameters by the additional liquid does not produce any decoupling from the properties of the electrophoretic liquid. These too also have to be set optimally for ionization in the electrospray method. Independence between electrophoresis and electrospray cannot therefore be achieved. Contrary to expectations, therefore, the method has no advantage.

On the other hand, the concentration of the substances to be analyzed is considerably reduced by the added liquid. The transfer yield of electrospray ions in the classic spray method into the vacuum of the mass spectrometer is extremely low, and only about 1/1,000 of the ions enter the mass spectrometer. The substance yield of this method is therefore very low.

This method is extremely complicated due to the adding of a second liquid, due to the obligatory exact setting of all the electrolytic parameters for this liquid, and due to the necessary pump and its setting, and cannot easily be made to operate in a stable manner.

SUMMARY OF THE INVENTION

The invention provides apparatus for the analysis of an analyte substance by capillary-electrophoresis separation and mass-spectrometric determination. The apparatus comprises an electrophoresis capillary having an inlet end and an outlet end. First and second electrophoresis electrodes are located, respectively, at the inlet end and the outlet end of the electrophoresis capillary, for applying an electrophoresis voltage to an analyte solution in the electrophoresis capillary. A power supply is provided for producing an electrophoresis voltage between the first and second electrophoresis electrodes.

A container is provided at the inlet end of the electrophoresis capillary for supplying a solution of the analyte substance to the electrophoresis capillary. A spray capillary has an inlet end located proximate to the outlet end of the electrophoresis capillary and an outlet end which is formed into a fine capillary tip, and receives solution discharged from outlet of the electrophoresis capillary. A spray counter-electrode is located adjacent to the tip of the spray capillary, and has an orifice by which ions produced in an electrospray process between the spray capillary and the counter-electrode can enter a mass spectrometer. A power supply is provided for producing a voltage between the spray capillary and the counter-electrode to cause the electrospraying of ions between the said spray capillary and the counter-electrode, and a decoupling chamber surrounds the electrophoresis capillary outlet and the spray capillary inlet, for decoupling the flow of solution discharged from the electrophoresis capillary from the spray capillary.

The supply container generally takes the form of a first liquid reservoir in which the inlet end of the electrophoresis capillary is located, and which also contains the first electrophoresis electrode. The decoupling chamber generally takes the form of a second liquid reservoir in which the outlet end of the electrophoresis capillary is located, and which also contains the second electrophoresis electrode.

The two capillaries are loosely coupled in the liquid of the second liquid reservoir, with a narrow gap between the end surfaces of the capillaries which handles the electric and hydrodynamic connection to the liquid of the reservoir. This loose coupling ensures that no forced flow becomes established in the microspray capillary but the flow can establish itself by self-regulation. It also ensures that electric current through the electrophoresis capillary and the current through the spray capillary, which is necessary for spraying, are decoupled from one another. In particular, the electrophoresis current does not have to be taken through the tip of the spray because at that point current density would be so high that the electrophoresis liquid might come to the boil. The voltage for microspraying depends on the voltage for electrophoresis and both can be optimally set independently of one another.

The gap between the electrophoresis capillary and the spray capillary is preferably about ¼ of the inside diameter of the electrophoresis capillary because this results in no increase in electric current density and no increase in substance-guiding field strength. Nor is there any excess warming of the electrolyte at this point.

The polarity of the migrating analyte ions in the electrophoresis capillary and that of the spray ions must be identical because only then does the electric spray current in the microspray capillary create a potential drop which guides the analyte ions to the tip of the spray capillary once they have entered the microspray capillary.

The inside diameter of the spray capillary should be small so that a relatively high velocity of flow is established which also carries many of the separated substance ions, which are emitted from the electrospray capillary, into the microspray capillary due to liquid friction, even if the higher field strength in the gap tends to conduct the ions out.

Preparation of the inside walls of the two capillaries should be the same or at least similar in order to create the same polarity of wall charges. The polarity of wall charges should correspond to the polarity of the migrating substance ions in order to obtain an optimal separation result. The end surfaces of the capillaries which form the gap should preferably also be prepared in this manner.

In this way over 20% of the analyte ions of interest can be transferred to the microspray capillary whilst the remainder migrates to the second liquid reservoir and is lost. At first glance this yield seems low because with the previous methods of coupling all the substance ions were fed to the electrospray process. However, since the yield of mass-spectrometrically usable ions in the microspray method is one hundred times larger than with the classic electrospray method, loose coupling achieves a substance ion gain of over twenty times.

It is a particular advantage of this coupling method that both the microspraying and capillary electrophoresis can easily be switched off electrically without separation being considerably disturbed. In particular, capillary gel electrophoresis has no detrimental effect on the separation capacity by interim switching off. The microspray can be switched off within a millisecond and also switched on within the same time. This means it is possible to meter the ions very accurately.

Due to the possibility of generating ions only when they are required, it is possible to once again reduce analyte consumption of the mass-spectrometric analysis by using storage mass spectrometers. Both with quadrupole ion trap and with ion cyclotron spectrometers only about 20 milliseconds are required to fill the storage cell with an adequate number of ions. For the mass-spectrometric analysis of the stored ions 100 milliseconds to one second are then required, depending on the necessary resolution and the type of analysis. By switching appropriately one can therefore achieve further substance savings of five to fifty times, albeit extending the total duration of analysis. By switching electrophoresis and spraying separately any intermediate value can also be achieved.

BRIEF DESCRIPTION OF THE DRAWINGS

A number of preferred embodiments of the invention are illustrated in the accompanying drawings, in which.

DETAILED DESCRIPTION OF THE PREFERRED EMBODIMENTS

Figure 1:
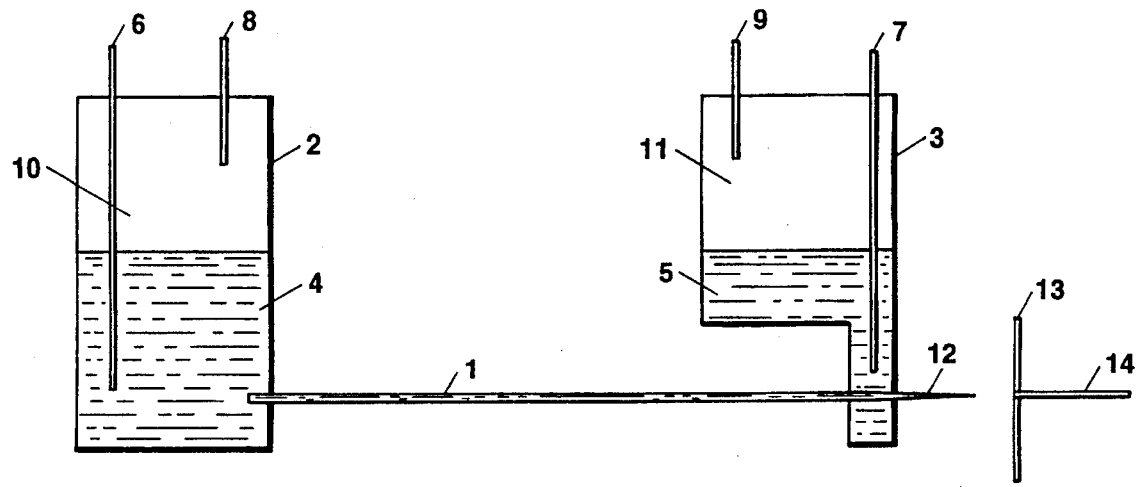
FIG. 1 is a general schematic representation of apparatus in accordance with the invention.

Referring first to FIG. 1, first and second liquid reservoirs 2, 3 are connected by an electrophoresis capillary 1. Reservoirs 2 and 3 and electrophoresis capillary 1 contain an electrophoresis liquid 4 and 5. First and second electrophoresis electrodes 6 and 7 are respectively located in reservoirs 2 and 3 at the inlet and outlet ends of the electrophoresis capillary 1 and can maintain a voltage between the two liquid reservoirs.

Two gas feeders 8 and 9 enable any desired gas pressure to be established in gas chambers 10 and 11 above the liquid in reservoirs 2,3. A spray capillary 12 has its inlet end in electrophoresis liquid 5 of liquid reservoir 3 and is arranged coaxially with electrophoresis capillary 1 and spaced from it by a short distance. The liquid reservoir 3 thus forms a decoupling chamber surrounding the outlet from electrophoresis capillary 1 and the inlet to the spray capillary 12. A spray jet is created by voltage between electrode 7 in the second liquid reservoir 3 and spray counter-electrode 13. The spray ions produced are able to enter the vacuum of the mass spectrometer through a fine entrance capillary 14.

Figure 2:
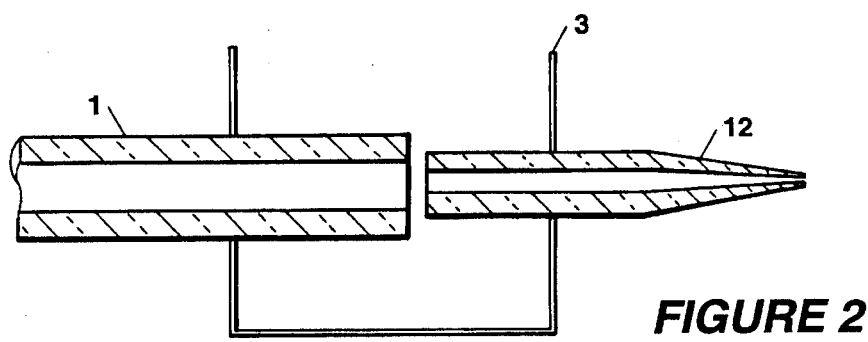
FIG. 2 shows an enlarged view of the spray capillary inlet region of FIG. 1.

FIG. 2 shows an enlargement of the loose coupling of electrophoresis capillary 1 with spray capillary 12 in liquid reservoir 3. The distance between the capillaries is only about ¼ of the inside diameter of the electrophoresis capillary 1.

Figure 3:
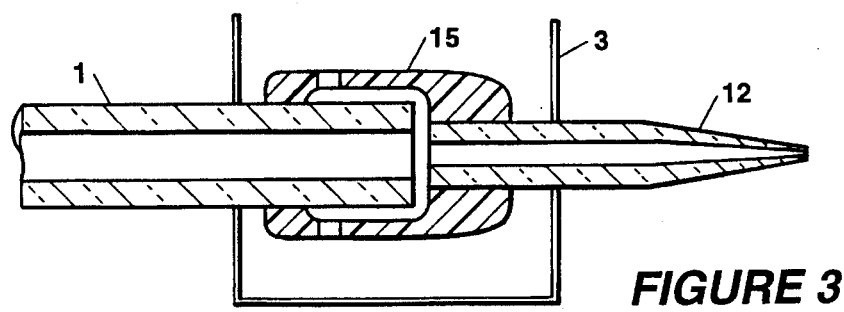
FIG. 3 shows an alternative arrangement for the spray capillary inlet region.

FIG. 3 shows an alternative loose coupling arrangement in which the ends of the two capillaries are surrounded by a retaining element 15 made of a suitable plastic, which, on the one hand, fixes the positions of capillaries 1 and 12 in relation to one another and, on the other hand, favourably conducts the liquid and the electric currents.

The electrophoresis capillary preferably has an inside diameter of about 50 micrometers and the spray capillary preferably has an inside diameter of about 20 micrometers, the gap being about 15 micrometers. For mass-spectrometric analyses the separation capacity does not have to be extremely high so usually a relatively short electrophoresis capillary with a length of about 20 centimeters is adequate, operated at a voltage of about 6 kilovolts. In the embodiment illustrated, the microspray capillary is only about two centimeters long and pulled out to a tip with an inside diameter of 2.5 micrometers. Flow velocity in the microspray capillary is then about one millimeter per second so the substance appears about 20 seconds after entering this capillary. An overpressure of approximately 100,000 Pascal in the gas chamber 11 of the second liquid reservoir 3 assists in maintaining the microspray with aqueous solutions.

The distance between the tip of the microspray capillary and the counter-electrode is optimally only about 1.5 millimetres. The counter-electrode contains the metallized end surface of an entrance capillary into a mass spectrometer, with an inside diameter of approximately 500 micrometers. The spray voltage is about 600 to 800 volts.

Particularly favourable for the positive spray ions which are normally analyzed is an embodiment of the electrophoresis capillaries made of silica glass, the interior of which is treated by aminopropylsilylation creating positive wall charges when the electrolytes are acidified. A formula is stated by Moseley et al.

A further favourable embodiment of the method is to generate liquid counterflow in the two capillaries by setting the pressures in the liquid reservoirs accordingly. This creates a relatively strong suction of liquid flow in the gap, which enhances transfer of the substance ions being examined into the microspray capillary. Electrophoresis then takes place in the electrophoresis capillary in the opposite direction to the flow of liquid.

It is favourable to provide the holder 15 for mutual fixing of the capillaries with a duct, the design of which is favourable for a high rate of substance transfer to the microspray capillary. It has become apparent that a deflexion of liquid current, as shown in FIG. 3, has a favourable effect.

What is claimed is:

1. Apparatus for the analysis of an analyte substance by capillary-electrophoresis separation and mass-spectrometric determination, which apparatus comprises:

an electrophoresis capillary having an inlet end and an outlet end;

first and second electrophoresis electrodes respectively located at the inlet end and the outlet end of the electrophoresis capillary, for applying an electrophoresis voltage to an analyte solution in the electrophoresis capillary;

a power supply for producing an electrophoresis voltage between the first and second electrophoresis electrodes;

a container at the inlet end of the electrophoresis capillary for supplying a solution of the analyte substance to the electrophoresis capillary;

a spray capillary having an inlet end located proximate to the outlet end of the electrophoresis capillary for receiving solution discharged from outlet of the electrophoresis capillary and having an outlet end which is formed into a fine capillary tip;

a spray counter-electrode adjacent the tip of the spray capillary, having an orifice by which ions produced in an electrospray process between the spray capillary and the counter-electrode can enter a mass spectrometer;

a power supply for producing a voltage between the spray capillary and the counter-electrode to cause the electrospraying of ions between the said spray capillary and the counter-electrode; and a decoupling chamber surrounding the electrophoresis capillary outlet and the spray capillary inlet, for decoupling the flow of solution discharged from the electrophoresis capillary from the spray capillary.

2. Apparatus as claimed in claim 1, wherein the voltage of the power supply for microspraying is connected between the said second electrophoresis electrode and the spray counter-electrode.

3. Apparatus as claimed in claim 2, wherein the spray capillary tip and the spray counter-electrode are separated by a distance of from 0.5 to 3 millimetres and wherein the spray voltage is from 500 to 1,200 volts.

4. Apparatus as claimed in claim 1, wherein the electrophoresis capillary has an inside diameter of from 25 to 100 micrometers and the electrospray capillary has an inside diameter of from 10 to 50 micrometers.

5. Apparatus as claimed in claim 1, wherein the decoupling chamber is closed and is provided with a gas supply pressure in order to positively influence the spraying at the spray capillary.

6. Apparatus as claimed in claim 1, wherein the gap between the electrophoresis capillary outlet and the spray capillary inlet is surrounded by an electrically insulating jacket adapted to conduct liquid leaving the electrophoresis capillary outlet to the region of the spray capillary inlet.

7. Apparatus as claimed in claim 6, wherein the jacket is such as to fix the spatial positions of the two capillaries relative to one another.

8. A method for the analysis of an analyte substance by capillary-electrophoresis separation and mass-spectrometric determination, which apparatus comprises:

separating a solution of the analyte substance by capillary electrophoresis in an electrophoresis capillary having an inlet end and an outlet end;

facilitating migration of separated analyte from the electrophoresis capillary into the inlet of a spray capillary having an inlet end located proximate to the outlet end of the electrophoresis capillary and having an outlet end which is formed into a fine capillary tip;

electrospraying the separated analyte from the fine capillary tip of the spray capillary by applying a voltage between the spray capillary and a counter-electrode to cause the electrospraying of ions between the said spray capillary and the counter-electrode, wherein the counter-electrode has an orifice by which ions produced in the electrospray process between the spray capillary and the counter-electrode can enter a mass spectrometer; and decoupling the flow of analyte in the electrophoresis capillary by means of a decoupling chamber surrounding the electrophoresis capillary outlet and the spray capillary inlet.

9. A method as claimed in claims 8 wherein in the distance of the spray capillary tip from the counter-electrode is from 0.5 to 3 millimetres and the voltage between the electrophoresis liquid and the counter-electrode is from 500 to 1,200 volts.

10. A method as claimed claim 8 wherein the electrophoresis capillary has an inside diameter of from 25 to 100 micrometers and the spray capillary has an inside diameter of from 10 to 50 micrometers.

11. A method as claimed in claim 8, further comprising lowering the electrospray voltage to cut off the flow of electrospray ions when the mass-spectrometric analysis requires no ion current.

12. A method as claimed in claim 8, wherein pressure is applied to the liquid in the decoupling chamber sufficient to influence positively the spraying process but wherein the pressure is not sufficient to cause liquid to emerge from the capillary tip when the spray voltage is switched off.

13. A method as claimed in claim 8, wherein the gap between the electrophoresis capillary outlet and the spray capillary inlet is surrounded by an electrically insulating jacket adapted to conduct liquid leaving the electrophoresis capillary outlet to the region of the spray capillary inlet.

14. A method as claimed in claim 13, wherein the jacket is such as to fix the spatial positions of the two capillaries relative to one another.

* * * * *